United States Patent [19]

Tsukashima et al.

[11] Patent Number: 5,484,949
[45] Date of Patent: Jan. 16, 1996

[54] METHOD FOR THE SYNTHESIS OF α β-UNSATURATED KETONES

[75] Inventors: Keiichi Tsukashima, Takaoka; Masashi Nakajima, deceased, late of Takaoka, by Michiko Nakajima, heir; Masayoshi Fujimaru; Kenji Suzuki, both of Takaoka, all of Japan

[73] Assignee: Nippon Soda Co., Ltd., Tokyo, Japan

[21] Appl. No.: 204,920

[22] Filed: Mar. 2, 1994

Related U.S. Application Data

[63] Continuation of Ser. No. 11,047, Jan. 29, 1993, abandoned.

[51] Int. Cl.$^6$ .................................................. C07D 307/16
[52] U.S. Cl. .................. 549/13; 549/78; 549/427; 549/498; 568/314; 568/346; 568/388
[58] Field of Search ................................ 568/314, 346, 568/388; 549/13, 78, 427, 498

[56] References Cited

U.S. PATENT DOCUMENTS

| | | | |
|---|---|---|---|
| 4,247,709 | 1/1981 | Rose et al. | 568/314 |
| 4,355,184 | 10/1982 | Kaku et al. | 568/388 |
| 5,428,174 | 6/1995 | Reissenweber et al. | 549/13 |

FOREIGN PATENT DOCUMENTS

| | | | |
|---|---|---|---|
| 3821197 | 12/1989 | Germany | 568/388 |

OTHER PUBLICATIONS

Grayson et al, J. Chem. Soc. Perkin Trans 1, pp. 2137–2142 (1986).

*Primary Examiner*—James H. Reamer
*Attorney, Agent, or Firm*—Joseph C. Mason, Jr.; George B. Oujevolk; Louise A. Foutch

[57] ABSTRACT

The present invention relates to a method for the synthesis of α, β-unsaturated ketones which comprises, in the method for the synthesis of α, β-unsaturated ketones represented by general formula $$R^1.CH=CH-\underset{\underset{O}{\|}}{C}-CH_3$$

reacting aldehydes represented by general formula $$R^1CHO$$

(where $R^1$ is as defined above) with alkali metal salt of acetoacetic acid represented by general formula $$CH_3\underset{\underset{O}{\|}}{C}CH_2COO^{\ominus}M^{\oplus}$$

(where $M^{\oplus}$ is an alkali metal ion), in the presence as a catalyst of 3-azabicyclo[3,2,2]nonane, a cyclic secondary amine represented by general formula (1)

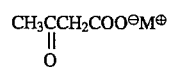

(1)

a cyclic secondary amine represented by general formula (2)

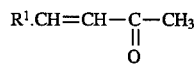

(2)

(where, 1 is 1 or more and up to 6, a ring with N is a 6-membered, 7-membered or 8-membered ring, the two neighbors of N are methylene, $R^3$ is a lower alkyl group, its substitution position is at a carbon atom other than two those adjacent to N, and

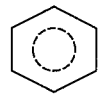

is an alicyclic group or a phenol group), or a secondary amine represented by general formula (3)

$$CH_3NHCH_2R^4 \qquad (3)$$

in a mixuture solvent of water and water-insoluble organic solvent, while keeping the pH constant with mineral acid, and by adjusting an amount of water.

7 Claims, No Drawings

METHOD FOR THE SYNTHESIS OF α β -UNSATURATED KETONES

This is a continuation of application Ser. No. 08/011,047 filed on Jan. 29, 1993 now abandoned.

FIELD OF INVENTION

This invention relates to a method for the preparation of α, β-unsaturated ketones represented by general formula [I]

$$R^1CH=CH-\underset{\underset{O}{\|}}{C}-CH_3 \quad [I]$$

(where $R^1$ is an aliphatic group with a side chain at the 1 position, an alicyclic group, a substituted alicyclic group, a heterocyclic group, a substituted heterocyclic group, a phenyl group or a substituted phenyl group) (hereinafter referred to as Compound [I]).

α, β-unsaturated ketones are very useful as intermediates for pharmaceuticals and agricultural chemicals.

DESCRIPTION OF RELATED ART

Various methods for the synthesis of unsaturated ketones using aldehyde as a starting material have been reported so far. These synthetic methods have various problems in industrial applications. For instance, in the aldol condensation of aldehyde with acetone, generally a large amount of byproducts is produced, isolation of the intended product is difficult, yield is low, and a very excessive amount of acetone is required.

In the synthetic method of condensing aldehyde and acetone using piperidineacetic acid as a catalyst [described in such documents as Indian J. Chem. Vol 16B, 970–972 (1978)], a large quantity of expensive catalyst is required, and a very excessive amount of acetone is necessary.

In the synthetic method that a Wittig reagent, which is obtained from the synthesis of monochloroacetone or monobromoacetone and triphenylphosphine, with aldehyde [described in such documents as Ber. 108, 2077 (1970)], the Wittig reagent of the material is expensive, and waste treatment is difficult. In the method that α, β-unsaturated β'-ketoester, which is obatined from the synthesis of aldehyde and tert-butyl acetoacetate, is pyrolyzed using p-toluenesulfonic acid as a catalyst at a high temperature [described in such documents as Acta Chem. Scand., 17, 2216–220 (1963)], synthesis yield is low in spite of low-temperature and many-hour synthesis of α, β-unsaturated β'-ketoester.

Synthesis yield is low in spite of many-hour reaction in the synthetic method that aldehyde and actone are reacted (U.S. Pat. No. 2,108,427).

In the method of Knoevenagel reaction of an alkaline metal salt of acetoacetic acid and aldehyde in the presence of aliphatic amine, which we applied before, (Japanese open patent No. Sho 57-4930), α, β-unsaturated ketone is obtained with good yield if the aldehyde has two hydrogen atoms at the α position. If no or one hydrogen atom at the α position, the reaction is extremely slow and yield is low. The aqueous solution of sodium acetoacetate obtained from hydrolysis of methylacetoacetate with sodium hydroxide is around 30% in concentration. When this aqueous solution and 3-ethylthiobutanal are reacted using piperidine as a catalyst and concentrated hydrochloric acid as a pH regulating agent, the intended α, β-unsaturated ketone is obtained with good yield of 90% or more. However, if an aldehyde branching at the α position for instance 3-tetrahydrothiopyran carbaldehyde, is reacted under the same conditions, the yield is low.

An object of this invention is to provide methods for the synthesis of α, β-unsaturated ketone with no or one hydrogen atom at the γ position, with good yield, in the reaction of alkaline metal salt of acetoacetate and aldehyde.

SUMMARY OF THE INVENTION

The inventors earnestly studied the aforementioned reaction of alkaline metal salt of acetoacetate and aldehyde with the aim of synthesis of α, β-unsaturated ketone with no or one hydrogen atom at the γ position, and found as the result that the low yield when such an aldehyde is reacted results from its steric hindrance and that the structure of the catalyst secondary amine and an amount of water in the system are factors to compensate for it. Thus this invention has been completed.

In other words, as a catalyst, the two carbons adjacent to N of secondary amine should be both methylene if the amine is cyclic and one of them be methyl if stright chain, and furthermore the amine be highly hydrophobic. Therefore, a water-soluble amine, such as piperidine, which is effective to aldehydes having two hydrogen atoms at the α position, is hardly effective to aldehydes with no or one hydrogen atom at the α position.

Diethylamine, dibutylamine and N-ethyl-n-laurylamine have an extremely small catalytic effect because one of the alkyl groups is not methyl.

An amount of water in the system is important and is required to be reduced. Methods to attain it are concentration of aqueous solution of alkaline metal salt of acetoacetic acid, and/or use of acid gas or acid anhydride or concentrated mineral acid with less water content, as an acid to maintain the pH, and/or a reaction while removing water to the outside of the system by azeotropic dehydration with water-insoluble solvent.

In addition, a combination of hydrophobicity of catalyst secondary amine and amount of water in the system is also important: When water is large in amount, a very hydrophobic catalyst should be used, but if an amount of water is small, a relatively less hydrophobic catalyst can be used.

DESCRIPTION OF THE PREFERRED EMBODIMENTS

This invention is a method for the synthesis of α, β-unsaturated ketones which comprises reacting materials, in the method for the synthesis of α, β-unsaturated ketches represented by generale formula [I]

$$R^1.CH=CH-\underset{\underset{O}{\|}}{C}-CH_3 \quad [I]$$

(wherein $R^1$ is an aliphatic group with a side chain at the 1 position, an alicyclic group, a substituted alicyclic group, a heterocyclic group, a substituted heterocyclic group, a phenyl group or a substituted phenyl group), using aldehydes represented by general formula [II]

$$R^1CHO \quad [II]$$

(where $R^1$ is as defined above) and alkaline metal salts of acetoacetic acid represented by general formula [III]

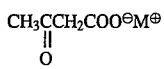 [III]

(where $M^{\oplus}$ is an alkaline metal ion) as catalysts, in the presence of 3-azabicyclo [3,2,2]nonane, a cyclic secondary amine represented by general formula (1)

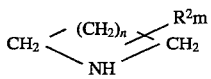 (1)

(where n is 3 or more and up to 5, m is 1 or more and up to 10, $R^2$ is an alkyl group having 1 to 10 carbon atoms and of straight chain or with side chains, an alkyl group substituted by alicyclic groups or phenyl groups, an alcyclic group which may be substituted by lower alkyl groups, or a phenyl group which may be substituted by lower alkyl groups, and an $R^2$ substitution position is at a carbon atom other than two those adjacent to N), a cyclic secondary amine represented by general formula (2)

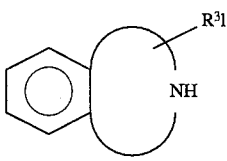 (2)

(where, l is 1 or more and up to 6, a ring containing N is a 6-membered, 7-membered or 8-membered ring, the two sides of N are methylene, $R^3$ is a lower alkyl group, its substitution position is at a carbon atom other than two those adjacent to N, and

is an analicyclic group or a phenyl group), or a secondary amine represented by general formula (3)

$CH_3NHCH_2R^4$ (3)

(where $R^4$ is an aliphatic group with a straight chain having 5 to 17 carbon atoms or with side chains, an alicyclic group which may be substituted by lower alkyl groups, a phenyl group which may be substituted by lower alkyl groups, or an alkyl group substituted by phenyl groups), in a mixture solvent of water and water-insoluble organic solvent, while keeping the pH constant with acid, and by adjusting an amount of water.

The α, β-unsaturated ketones represented by general formula [I] and which are the objects of synthesis in this invention are α, β-unsaturated ketones having aliphatic groups with side chains such as 5-methyl-3-hexene-2-one, 5-methyl-3-heptene-2-one, 5-methyl-3-octene-2-one, 5,6-dimethyl-3-heptene-2-one, 5-methyl-3-nonene-2-one, 5-ethyl-3-nonene-2-one, 5-ethyl-3-octene-2-one, 5-methyl-3-decene-2-one, 5-methyl-3-undecene-2-one and 5-methyl-3-undecene-2-one; α, β-unsaturated ketones having alicyclic groups such as 4-cyclohexyl-3-butene-2-one, 4-(2-methylcyclohexyl)-3-butene-2-one, 4-(3-methylcyclohexyl)-3-butene-2-one and 4-(4-methylcyclohexyl)- 3-butene-2-one; α, β-unsaturated ketones having heterocyclic groups such as 4-(3-tetrahydropyranyl)-3-butene-2-one, 4-(4-tetrahydropyranyl)-3-butene-2-one, 4-(2-tetrahydrofuranyl)-3-butene-2-one and 4-(3-tetrahydrothiopyranyl)- 3-butene-2-one; and α,β-unsaturated ketones having phenyl groups with substituents such as 4-phenyl-3-butene-2-one, 4-(3-methylphenyl)-3-butene-2-one, 4-(2-methylphenyl)-3-butene-2-one, 4-(4-methylphenyl)-3-butene-2-one, 4-(4-methylthiophenyl)-3-butene-2-one and 4-(4-chlorophenyl)-3-butene-2-one.

One material, the aldehyde represented by general formula [II], is an aldehyde with no or one hydrogen atom at the α position includes aliphatic aldehydes branched at the α position of aldehyde such as isobutylaldehyde, 2-methylbutanal, 2-methylpentanal, 2,3-dimethylbutanal, 2-methylhexanal, 2-ethylhexanal, 2-ethylpentanal, 2-methylheptanal and 2-methylnonal; aldehydes having alicyclic groups such as cyclohexane carbaldehyde, 2-methylcyclohexane carbaldehyde, 3-methylcyclohexane carbaldehyde and 4-methylcyclohexane carbaldehyde; heterocyclic aldehydes such as 4-tetrahydropyran carbaldehyde, 2-tetrahydrofuran carbaldehyde, 3-tetrahydropyran carbaldehyde and 3-tetrahydrothiopyran carbaldehyde; and aromatic aldehydes such as benzaldehyde, o-methylbenzaldehyde, m-methylbenzaldehyde, p-methylbenzaldehyde, p-methylthiobenzaldehyde and p-chlorobenzaldehyde.

The other material, alkaline metal salt of acetoacetic acid, represented by general formula [III] is sodium acetoacetate, potassium acetoacetate, and lithium acetoacetate. An aqueous solution of alkaline metal salt of acetoacetic acid is easily obtained by hydrolysis of diketene or acetoacetates in an aqueous solution of hydroxide alkaline solution such as sodium hydroxide or potassium hydroxide. The solution can be highly concentrated under reduced pressure.

The catalyst secondary amines represented by general formula (1) include piperidines such as 3,5-dimethylpiperidine, 3-butylpiperidine, 4-butylpiperidine, 3-hexylpiperidine, 4-hexylpiperidine, 3-cyclohexylpiperidine, 4-cyclohexylpiperidine, 4-benzylpiperidine, 3-benzylpiperidine and 4-phenylpiperidine; and cyclic amines such as hexamethyleneimine, heptamethyleneimine and 3,3,5-trimethylhexahydroazepine. The two carbons adjacent to N must be both methylene.

The cyclic secondary amines represented by general formula (2) include cyclic amines such as 1,2,3,4-tetrahydroisoquinoline, perhydroisoquinoline, 4-methylperhydroisoquinoline and 4-ethylperhydroisoquinoline.

The secondary amines represented by general formula (3) include N-methylhexylamine, N-methyloctylamine, N-methyldecylamine, N-methyl-2-ethylhexylamine, N-methyloctyldecylamine, N-methyl-2-methyloctylamine, N-methylcyclohexylmethylamine and N-methylbanzylamine, being secondary amines of which one of groups bonding to N is a methyl group and the other is methylene.

These catalyst secondary amines including 3-azabicyclo [3,2,2]nonane are used in combination of amount of water of the system: When a concentrated aqueous solution of alkaline metal salt of acetoacetic acid is used, relatively less hydrophobic secondary amines such as 4-methylpiperidine to very hydrophobic secondary amines such as N-methyldecylamine can be employed. When the alkaline metal salt of acetoacetic acid is low in concentration, very hydrophobic amines such as 3-hexylpiperidine or N-methyldecylamine are selected.

Methods to reduce the amount of water in the system are, in addition to use of concentrated aqueous solution of alkaline metal salt of acetoacetic acid, use of acid gas such as hydrogen chloride gas, or acid anhydride such as anhydrous sulfuric acid or phosphorus pentaoxide, or concentrated acid such as concentrated sulfuric acid or 85% phosphoric acid, as an acid to control the pH, or removal of water to the outside of the system by azeotropic dehydration with water-insoluble solvent during the reaction.

Water-insoluble organic solvents used in this reaction include chlorinated hydrocarbon solvents such as dichloromethane, chloroform and dichloroethane; and aromatic solvents such as benzene, toluene and xylene.

A way of implementing the synthetic method of this invention is described in detail:

To an aqueous solution of 1 to 3 moles of alkaline metal salt of acetoacetic acid to a mole of aldehyde was added 0.01 moles or more, preferebly 0.05 to 0.20 moles, to a mole of aldehyde, of catalyst secondary amine selected by taking into account the concentrations of alkaline metal salt of acetoacetic acid and of mineral acid used to adjust the pH, and further a mineral acid is added to adjust the pH to 6.0 to 8.0.

Then 10 to 500 ml/mole (of aldehyde) of water-insoluble organic solvent is added together with aldehyde. If no solvent is used, β-hydroxyketone represented by general formula [IV] and described later is byproduced in a large amount, though the reaction proceeds. The reaction is carried out with stirring for 1 to 8 hours at 30° to 60° C. while keeping the pH to 6.0 to 8.0 with mineral acid. As the acid, in order not to increase the amount of water in the system, acids with less water content such as concentrated sulfuric acid and 85% phosphoric acid, or acid gas such as hydrogen chloride gas, or anhydrous acids such as anhydrous sulfuric acid and phosphorus pentaoxide are preferably used, if the aqueous solution of alkaline metal salt of acetoacetic acid is around 30% in concentration. If the aqueous solution of alkaline metal salt of acetoacetic acid is 50% or more in concentration, an acid with much water content such as concentrated hydrochloric acid may be used. It is possible to use an acid with much water content such as concentrated hydrochloric acid in a manner of removing water to the outside of the system during the reaction by azeotropic dehydration with water-insoluble solvent, if the concentration of alkaline metal salt of acetoacetic acid is around 30%. After the reaction is completed, water and water-insoluble organic solvent are added, the pH is adjusted to below 2 with mineral acid, and the organic layer is separated from the aqueous layer. The organic layer is concentrated, and the obtained residue is distilled under reduced pressure to give the intended α, β-unsaturated ketone. β-hydroxyketones represented by general formula [IV]

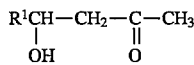

[IV]

(where $R^1$ is as defined above) may be byproduced in lees than 10%, depending on a combination of aldehyde, catalyst and an amount of water in the system. If so, after the reaction is completed, 0.10 to 2.00 moles, to aldehyde, of mineral acid such as sulfuric acid is added to the reaction mixture to heat, then the compounds represented by general formula [IV] can be converted to the intended α,β-unsaturated ketone.

The aqueous layer separated from the organic layer is adjusted the pH to 13 or more with hydroxide alkali such as sodium hydroxide and extracted with water-insoluble organic solvent to recover 90% or more of the catalyst amine used. The recovered can be used again.

EXAMPLES

Implementation manner of this invention is further described in detail by reference to the following examples. The range of this invention is not limited at all by the following examples.

Example 1

Into a reaction vessel of 500 ml in inside volume were placed 116.0 g 1.0 mole) of methyl acetoacetate and 102.5 g of water, to which 144.3 g (1.05 moles) of 29.1% NaOH aqueous solution was dropped over an hour with stirring while cooling with water and keeping the inside temperature to below 35° C., and after it the resulting solution was continuously stirred at 33° to 37° C. for 6 hours. Then water and methanol were distilled by aspirator at 40° C. under reduced pressure. Part of the content in the flask was collected to titrate for pH with 1N-HCl standard aqueous solution. The obtained aqueous solution of sodium acetoacetate was 40% in concentration and the yield was 96.5% to methyl acetoacetate. 62.1 g (0.20 moles) of the aqueous solution of sodium acetoacetate was placed in a reaction vessel of 200 ml in inside volume, 1.13 g (0.01 moles) of 3,5-dimethylpiperidine was added and concentrated sulfuric acid was added to adjust the pH to 7.0. Into the resulting solution were added 10 ml of chloroform and 7.2 g (0.10 moles) of isobuthylaldehyde to react at 40° C. for 5 hours. The pH was maintained to 7.0 to 7.5 during the reaction with concentrated sulfuric acid. After the reaction was completed, 10 ml of water and 20 ml of chloroform were added, the pH was adjusted to 1.5 with concentrated sulfuric acid, the organic layer was separated form the aqueous layer, and the solvent was distilled under reduced pressure. The remaining oily product was distilled under reduced pressure to give 9.9 g of colorless oily product with boiling point of 61° to 64° C. (28 mmHg) and $N^1{}_D^{6.5}$ 1.4439. (Crude yield: 88.7%) The obtained product was analyzed by gas chromatography to find that the intended product 5-methyl-3-hexene-2-one was 97.9% in purity. (Yield: 86.8%) 1.5% of a byproduct, 4-hydroxy-5-methylhexane-2-one, was contained.

Examples 2 and 3

Example 1 was repeated except using 2-ethylhexanal or cyclohexane carbaldehyde instead of isobutylaldehyde. The results are shown in Table 1.

Example 4

46.5 g (0.15 moles) of 40% aqueous solution of sodium acetoacetate synthesized under the same conditions as those of Example 1 was placed in a reaction vessel of 100 ml in inside volume, 1.13 g (0.01 moles) of 3,5-dimethylpiperidine was added, and the pH was adjusted to 7.0 with concentrated sulfuric acid. Into the resulting solution were added 10 ml of chloroform and 11.4 g of 4-tetrahydropyran carbaldehyde to react at 40° C. with stirring. The pH was maintained to 7.0 to 7.5 during the reaction by dropping concentrated sulfuric acid. After the reaction was completed, 10 ml of water and 40 ml of chloroform were added, the pH was adjusted to 1.5 with concentrated sulfuric acid, the organic layer was separated from the aqueous layer, and the solvent was distilled under reduced pressure. The remaining oily product was distilled under vacuum to give 15.0 g of colorless oily product with boiling point od 91° to 95° C. (0.1 mmHg). (Crude yield: 97.2%) The obtained product was analyzed by gas chromatography to find that the intended product 4-(4-tetrahydropyranyl)-3-butene-2-one was 90.8% in purity. (Yield: 88.3%) 9.1% of a byproduct, 4-hydroxy-4-(4-tetrahydropyranyl)-butane-2-one was contained.

The same reaction was repeated. After the reaction was completed, 5.9 g of concentrated sulfuric acid and 30 ml of chloroform were added to the reaction mixture to heat to reflux at about 60° C. for 2 hours. After cooled, 20 ml of water was added, the organic layer was separated and washed with water, and the solvent was distilled under reduced pressure. The remaining oily product was distilled under vacuum to give 15.4 g of colorless oily product. (Crude yield: 99.6%) The obtained product was analyzed by gas chromatography to find that the intended product 4-(4-tetrahydropyranyl)-3-butene-2-one was 96.8% in purity. (Yield: 96.4%) The product, if let stand at room temperature, crystallized. The crystal had melting point of 42° to 46° C.

Examples 5 through 34, and Comparative Examples 1 through 6

Example 1 or 4 was repeated using different aldehyde and catalyst secondary amine under the conditions shown in Table 1. Those for Comparative Examples 1 to 6 are shown in Table 2.

Example 35

The aqueous solution of sodium acetoacetate which was obtained by hydrolysis of aqueous sodium hydroxide solution of methylacetoacetate according to the method of Example 1 was 32% in concentration. 93.0 g (0.24 moles) of the aqueous solution was placed in a redaction vessel of 200 ml in inside volume, 2.26 g (0.02 moles) of 3,5-dimethylpiperidine was added, and pH was adjusted to 7.0 with concentrated hydrochloric acid. Into the resulting solution were added 20 ml of toluene and 26.0 g (0.20 moles) of 3-tetrahydrothiopyrane carbaldehyde, and a mixture of toluene and water was distilled by aspirator under reduced pressure at an inside temperature of 40° C. During the distillation, the pH was adjusted to 7.0 to 7.5 with concentrated hydrochloric acid and the same amount of toluene as that of toluene distilled was continuously added into the reaction vessel so that the amount of toluene in the vessel was always about 20 ml. After 5 hours, the same post treatment as that used in Examaple 4 was carried out to give the intended product of 4-(3-tetrahydrothiopyranyl)-3-butene-2-one with yield of 88.2%.

Example 36

93.0 g (0.24 moles) of 32% aqueous solution of sodium acetoacetate obtained in the same manner as that used in Example 35 was placed in a reaction veseel of 200 ml in inside volume, 22.6 g (0.02 moles) of 3,5-dimethylpiperidine was added, an pH was adjusted to 7.0 with concentrated hydrochloric acid. Into the resulting solution were added 20 ml of toluene and 26.0 g (0.20 moles) of 3-tetrahydrothiopyran carbaldehyde to react at 40° C. for 5 hours with stirring. During the reaction, hydrogen chloride gas was blown into the reaction solution in order to keep the pH in the range of 7.0 to 7.5. After the reaction was completed, the solution was treated in the same manner as that used in Example 4. 4-(3-Tetrahydrothiopyranyl)- 3-butene-2-one was obtained with yield of 89.5%. Boiling point: 107°–108° C. (0.12 mmHg)

Example 37

93.0 g (0.24 moles) of 32% aqueous solution of sodium acetoacetate obtained in the same manner as that used in Example 35 was placed in a reaction veseel of 200 ml in inside volume, 2.26 g (0.02 moles) of 3,5-dimethylpiperidine was added, and the pH was adjusted to 7.0 with concentrated sulfuric acid. Into the resulting solution were added 20 ml of toluene and 13.0 g (0.10 moles) of 3-tetrahydrothiopyran. carbaldehyde to react at 40° C. for 5 hours with stirring. During the reaction, liquid sulfar trioxide ion was dropped during the reaction solution in order to keep the pH in the range of 7.0 to 7.5. After the reaction was completed, the same post treatment as that used in Example 4 was carried out to give 4-(3-Tetrahydrothiopyranyl)-3-butene-2-one with yield of 88.9%. Boiling point: 106°–108° C. (0.10 mmHg)

TABLE 1

| Compound No. | material R¹CHO R¹ | product R¹CH=CHCOCH₃ | Catalytic amine mole ratio (/aldehyde) | Concentration, mole ratio of aqueous solution of sodium acetoacetate (/aldehyde) | solvent (ml/mole of aldehyde) | pH adjusting agent | Reaction temperature Reaction Time | yield No dehydration | yield with dehydration | Physical property value |
|---|---|---|---|---|---|---|---|---|---|---|
| 1 | $CH_3\text{-}CH\text{-}CH_3$ (isopropyl) |  | 3,5-dimethylpiperidine 0.10 | 40 2.0 | chloroform 100 | C.H₂SO₄ | 40° C. 5 hr | 86.8 |  | bp. 61–64° C. (28 mmHg) $n_D^{16.5}$ 1.4439 |
| 2 | $CH_2CH_2CH_2CH\text{-}C_2H_5$ |  | 3,5-dimethylpiperidine 0.10 | 40 2.0 | chloroform 100 | C.H₂SO₄ | 50° C. 8 hr | 89.7 |  | bp. 63–65° C. (0.9 mmHg) $n_D^{25.5}$ 1.4513 |
| 3 | cyclohexyl |  | 3,5-dimethylpiperidine 0.10 | 40 1.5 | chloroform 100 | C.H₂SO₄ | 40° C. 3 hr | 95.8 |  | bp. 57–58° C. (0.3 mmHg) $n_D^{13.5}$ 1.4861 |
| 4 | 4-methyltetrahydropyran-4-yl |  | 3,5-dimethylpiperidine 0.10 | 40 1.5 | chloroform 100 | C.H₂SO₄ | 40° C. 3 hr | 88.3 | 96.4 | bp. 91–95° C. (0.1 mmHg) mp. 45–46° C. |
| 5 | 4-methyltetrahydropyran-4-yl |  | 3,5-dimethylpiperidine 0.10 | 40 1.5 | chloroform 100 | C.H₂SO₄ | 40° C. 3 hr | 89.6 | 95.3 | bp. 102–103° C. (2 mmHg) $n_D^{26}$ 1.4783 |
| 6 | 2-methyltetrahydropyran-2-yl |  | 3,5-dimethylpiperidine 0.10 | 40 1.5 | chloroform 100 | C.H₂SO₄ | 40° C. 4 hr | 83.4 | 92.4 | bp. 92–93° C. (5 mmHg) $n_D^{25}$ 1.4709 |
| 7 | 2-methyltetrahydrofuran-2-yl |  | 3,5-dimethylpiperidine 0.10 | 40 1.3 | chloroform 100 | C.H₂SO₄ | 40° C. 3 hr | 90.3 | 96.1 | bp. 78–81° C. (3 mmHg) $n_D^{25}$ 1.4820 |
| 8 | 2-methyltetrahydrothiopyran-2-yl |  | 3,5-dimethylpiperidine 0.10 | 40 1.2 | toluene 100 | C.H₂SO₄ | 40° C. 3 hr. | 89.8 | 92.2 | bp. 107–108° C. (0.1 mmHg) $n_D^{22}$ 1.5320 |

TABLE 1-continued

| Compound No. | R¹ material R¹CHO | product R¹CH=CHCOCH₃ | Catalytic amine mole ratio (/aldehyde) | Concentration, mole ratio of aqueous solution of sodium acetoacetate (/aldehyde) | solvent (ml/mole of aldehyde) | pH adjusting agent | Reaction temperature Reaction Time | yield No dehydration | yield with dehydration | Physical property value |
|---|---|---|---|---|---|---|---|---|---|---|
| 9 | 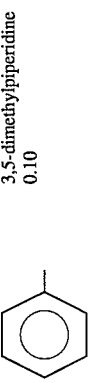 | | 3,5-dimethylpiperidine 0.10 | 40 1.5 | chloroform 100 | C.H₂SO₄ | 50° C. 6 hr. | 91.6 | 97.9 | bp. 81–95° C. (0.6 mmHg) mp. 41–42° C. |
| 10 | 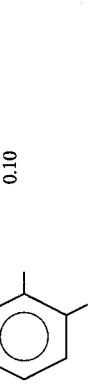 | | 3,5-dimethylpiperidine 0.10 | 40 2.5 | chloroform 100 | C.H₂SO₄ | 50° C. 12 hr. | 88.3 | 91.3 | bp. 96–96.5° C. (0.1 mmHg) $n_D^{20}$ 1.5881 |
| 11 | 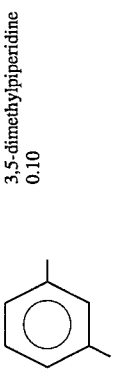 | | 3,5-dimethylpiperidine 0.10 | 40 2.0 | chloroform 100 | C.H₂SO₄ | 50° C. 5 hr. | 90.2 | 96.9 | bp. 101.5–106° C. (0.2 mmHg) $n_D^{20}$ 1.5869 |
| 12 | 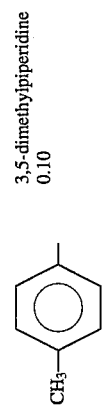 | | 3,5-dimethylpiperidine 0.10 | 40 2.0 | chloroform 100 | C.H₂SO₄ | 40° C. 5 hr. | 95.7 | | |
| 13 | 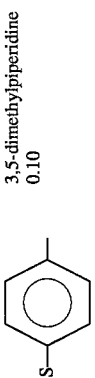 | | 3,5-dimethylpiperidine 0.10 | 40 2.0 | chloroform 100 | C.H₂SO₄ | 50° C. 7 hr. | 91.9 | | mp. 103.5–106° C. |
| 14 | 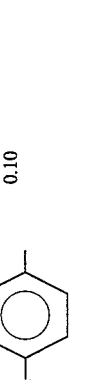 | | 3,5-dimethylpiperidine 0.10 | 40 2.0 | chloroform 100 | C.H₂SO₄ | 50° C. 6 hr. | 85.4 | 91.6 | bp. 105–108° C. (0.7 mmHg) mp. 60–63.5° C. |
| 15 |  | | 4-methylpiperidine 0.1 | 65 1.2 | chloroform 200 | C.HCl | 40° C. 6 hr | 87.4 | 93.3 | |
| 16 |  | | 3-methylpiperidine 0.1 | 65 1.2 | chloroform 200 | C.HCl | 40° C. 6 hr | 87.0 | 93.3 | |

TABLE 1-continued

| Compound No. | R¹ material R¹CHO | product R¹CH=CHCOCH₃ | Catalytic amine | mole ratio (/aldehyde) | Concentration, mole ratio of aqueous solution of sodium acetoacetate (/aldehyde) | solvent (ml/mole of aldehyse) | pH adjusting agent | Reaction temperature Reaction Time | yield No dehydration | yield with dehydration | Physical property value |
|---|---|---|---|---|---|---|---|---|---|---|---|
| 17 | CH₃—CH(—CH₃) | | 3-n-butylpiperidine | 0.1 | 32 1.2 | toluene 100 | C.H₂SO₄ | 40° C. 6 hr | 82.5 | 90.0 | |
| 18 | CH₃—CH(—CH₃) | | 4-n-butylpiperidine | 0.1 | 32 1.2 | toluene 100 | C.H₂SO₄ | 40° C. 6 hr | 82.5 | 89.6 | |
| 19 | CH₃—CH(—CH₃) | | 3-n-hexylpiperidine | 0.1 | 32 1.2 | toluene 100 | C.H₂SO₄ | 40° C. 6 hr | 78.6 | 84.4 | |
| 20 | CH₃—CH(—CH₃) | | 4-n-hexylpiperidine | 0.1 | 40 1.2 | toluene 100 | C.H₂SO₄ | 40° C. 6 hr | 82.6 | 86.7 | |
| 21 | CH₃—CH(—CH₃) | | 3-cyclohexylpiperidine | 0.1 | 32 1.2 | toluene 100 | C.H₂SO₄ | 40° C. 6 hr | 82.7 | 90.4 | |
| 22 | CH₃—CH(—CH₃) | | 4-cyclohexylpiperidine | 0.1 | 32 1.0 | toluene 100 | C.H₂SO₄ | 40° C. 6 hr | 82.2 | 87.8 | |
| 23 | CH₃—CH(—CH₃) | | 3-cyclohexylmethyl piperidine | 0.1 | 32 1.0 | toluene 100 | C.H₂SO₄ | 40° C. 6 hr | 80.4 | 87.6 | |
| 24 | CH₃—CH(—CH₃) | | 4-benzylpiperidine | 0.1 | 32 1.0 | toluene 100 | C.H₂SO₄ | 40° C. 6 hr | 82.1 | 90.3 | |

TABLE 1-continued

| Compound No. | R¹ material R¹CHO | R¹ product R¹CH=CHCOCH₃ | Catalytic amine mole ratio (/aldehyde) | Concentration, mole ratio of aqueous solution of sodium acetoacetate (/aldehyde) | solvent (ml/mole of aldehyde) | pH adjusting agent | Reaction temperature Reaction Time | yield No dehyd ration | yield with dehyd ration | Physical property value |
|---|---|---|---|---|---|---|---|---|---|---|
| 25 | CH₃–CH–CH₃ | | 4-phenylpiperidine 0.1 | 32 1.0 | toluene 100 | C.H₂SO₄ | 40° C. 6 hr | 82.2 | 86.8 | |
| 26 | CH₃–CH–CH₃ | | perhydroisoquinoline 0.1 | 32 1.0 | toluene 100 | C.H₂SO₄ | 40° C. 6 hr | 84.7 | 90.0 | |
| 27 | CH₃–CH–CH₃ | | 1,2,3,4-tetrahydro isoquinoline 0.1 | 32 1.0 | toluene 100 | C.H₂SO₄ | 40° C. 8 hr | 75.1 | 81.3 | |
| 28 | CH₃–CH–CH₃ | | 3,3,5-trimethylhexa hydroazepine 0.1 | 32 1.0 | toluene 100 | C.H₂SO₄ | 40° C. 8 hr | 75.7 | 85.4 | |
| 29 | CH₃–CH–CH₃ | | 3-azabicyclo (3,2,2)- nonan 0.1 | 32 1.0 | toluene 100 | C.H₂SO₄ | 40° C. 8 hr | 79.3 | 85.1 | |
| 30 | CH₃–CH–CH₃ | | N-methylhexylamine 0.1 | 32 1.2 | toluene 100 | C.H₂SO₄ | 40° C. 8 hr | 73.4 | 83.3 | |
| 31 | CH₃–CH–CH₃ | | N-methyl-2- ethylhexylamine 0.1 | 32 1.2 | toluene 100 | C.H₂SO₄ | 40° C. 8 hr | 75.7 | 85.1 | |
| 32 | CH₃–CH–CH₃ | | N-methylbenzylamine 0.1 | 32 1.2 | toluene 100 | C.H₂SO₄ | 40° C. 8 hr | 71.9 | 77.5 | |

TABLE 1-continued

| Compound No. | R¹ material R¹CHO | product R¹CH=CHCOCH₃ | Catalytic amine mole ratio (/aldehyde) | Concentration, mole ratio of aqueous solution of sodium acetoacetate (/aldehyde) | solvent (ml/mole of aldehyde) | pH adjusting agent | Reaction temperature Reaction Time | yield No dehydration | yield with dehydration | Physical property value |
|---|---|---|---|---|---|---|---|---|---|---|
| 33 |  | | N-methylcyclohexyl methylamine 0.1 | 32 1.2 | toluene 100 | C.H₂SO₄ | 40° C. 8 hr | 76.5 | 83.5 | |
| 34 |  | | N-methyloctadecyamine 0.1 | 4.0 1.2 | toluene 100 | C.H₂SO₄ | 40° C. 4 hr | 72.5 | 79.5 | |
| 35 | 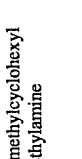 | | 3,5-dimethylpiperidine 0.1 | 32 1.2 | toluene 100 | C.HCl | 40° C. 5 hr | 88.2 | 91.5 | |
| 36 | 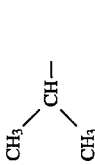 | | 3,5-dimethylpiperidine 0.1 | 32 1.2 | toluene 100 | HClgas | 40° C. 5 hr | 89.5 | | |
| 37 |  | | 3,5-dimethylpiperidine 0.1 | 32 1.2 | toluene 100 | SO₃ | 40° C. 5 hr | 88.9 | | |

TABLE 2

| Compound No. | R¹ material aldehyde R¹CHO | product R¹CH=CH—C—CH₃ ‖ O | Catalytic amine | mole ratio (/aldehyde) | Aqueous solution of sodium acetoacetate concentration wt % | mole ratio/ aldehyde | Solvent | ml/mole of aldehyde | pH adjusting agent (C stands for conc.) | Reaction temperature reaction time | Yield (%) to aldehyde (no dehydration) |
|---|---|---|---|---|---|---|---|---|---|---|---|
| 1 | CH₃CH₂CH₂— \| C₂H₅S (2H at the α-position) | | piperidine | 0.06 | 32 | 1.2 | toluene | 170 | C.HCl | 30° C. 6 Hr | 93.5 |
| 2 | (thiane ring with CH₂ substituent) | | piperidine | 0.06 | 32 | 1.2 | toluene | 170 | C.HCl | 30° C. 4 Hr | 39.0 |
| 3 | CH₃CH₂CH₂— \| C₂H₅S (2H at the α-position) | | dibuthylamine | 0.10 | 32 | 1.2 | toluene | 170 | C.HCl | 30° C. 3 Hr | 88.0 |
| 4 | (thiane ring with CH₂ substituent) | | dibuthylamine | 0.10 | 32 | 1.2 | toluene | 170 | C.HCl | 30° C. 4 Hr | 15.0 |
| 5 | (thiane ring with CH₂ substituent) | | 2-methylpiperidine | 0.10 | 32 | 1.2 | toluene | 100 | C.H₂SO₄ | 40° C. 6 Hr | 4.6 |
| 6 | (thiane ring with CH₂ substituent) | | N-methylcyclohexylamine | 0.10 | 40 | 1.2 | toluene | 100 | C.H₂SO₄ | 40° C. 3 Hr | 13.4 |

INDUSTRIAL APPLICABILITY

This invention is to provide methods for the synthesis of intended α, β-unsaturated ketones with no or one hydrogen atom at the γ position with high yield under mild reaction conditions, by reacting an aqueous solution of alkaline metal salt of acetoacetic acid with aldehydes with no or one hydrogen atom at the α position in the presence of secondary amine with restricted structure as a catalyst by adjusting an amount of water in the system. The invention is extremely significant in industry, particularly in manufacturing of agricultural chemicals and pharmaceuticals.

We claim:

1. A method for preparing α,β-unsaturated ketone which consists essentially of reacting a compound of the formula $$R^1CHO$$

wherein $R^1$ is a heterocyclic group, or a substituted heterocyclic group, with the proviso that said compound cannot contain more than one α-hydrogen with an alkali metal salt of a formula

wherein $M^\oplus$ is an alkali metal ion; and, wherein the reaction is carried out in the presence of a catalytic amount of a compound selected from the group consisting of (1) 3-azabicyclo (3,2,2) nonane, (2) a cyclic secondary amine of the general formula (1)

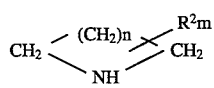 (1)

wherein n is 3, 4, or 5, m is 1, 2, 3, 4, 5, 6, 7, 8, 9 or 10, and, $R^2$ is (a) an alkyl group having from 1–10 carbon atoms and of straight chain or with side chains, (b) an alkyl group substituted by alicyclic groups or with phenyl groups, (c) an alicyclic group optionally substituted by lower alkyl groups, or, (d) a phenyl group optionally substituted by lower alkyl groups, with the proviso that the $R^2$ substitution position is at a carbon atom other than those adjacent to N; and, (3) a cyclic secondary amine of the formula (2)

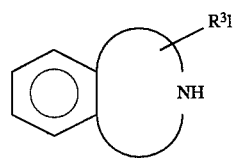 (2)

wherein l is 1, 2, 3, 4, 5, or 6, a ring with N is 6-membered, 7-membered, or 8-membered ring, the two adjacent positions of N are methylene, $R^3$ is a lower alkyl group with the proviso that its substitution position is at a carbon atom other than those adjacent to N, and,

is an alicyclic group or a phenyl group; and, (4) a secondary amine of the formula (3)

$$CH_3NHCH_2R^4$$

wherein $R^4$ is (a) an aliphatic group having 5–17 carbon atoms and of straight chain or with side chains, (b) an alicyclic group optionally substituted by lower alkyl groups, (c) a phenyl group optionally substituted by lower alkyl groups, or (d) an alkyl group substituted by phenyl groups, in a solvent comprising a mixture of water and water insoluble organic solvent under conditions of controlled pH and controlled water content to yield a compound of the formula

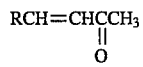

wherein R is a heterocyclic group, or a substituted heterocyclic group.

2. A method for preparing α,β-unsaturated ketone which consists essentially of reacting a compound of the formula $$R^1CHO$$

wherein $R^1$ is a heterocyclic group, with the proviso that said compound cannot contain more than one α-hydrogen with an alkali metal salt of a general formula

wherein $M^\oplus$ is an alkali metal ion, in the presence of a catalytic amount of secondary amine catalyst selected from the group consisting of 3, 5,-dimethylpiperidine, 3-butylpiperidine, 4-butylpiperidine, 3-hexylpiperidine, 4-hexylpiperidine, 3-cyclohexylpiperidine, 4-cyclohexylpiperidine, 4-benzylpiperidine, 3-benzylpiperidine, and 4-phenylpiperidine; in a solvent comprising a mixture of water and water insoluble organic solvent under conditions of controlled pH and controlled water content to yield a compound of the formula

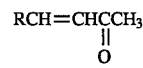

wherein R is a heterocyclic group.

3. A method of preparing α,β-unsaturated ketone which consists essentially of reacting a compound of the formula $$R^1CHO$$

wherein $R^1$ is selected from the group consisting of

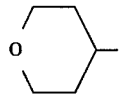

-continued

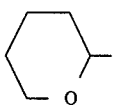

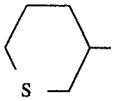

and, with an alkali metal salt of the formula

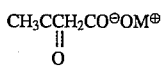

wherein $M^{\oplus}$ is an alkali metal ion, in the presence of a secondary amine catalyst selected from the group consisting of 3,5,-dimethylpiperidine, 3-butylpiperidine, 4-butylpiperidine, 3-hexylpiperidine, 4-hexylpiperidine, 3-cyclohexylpiperidine, 4-cyclohexylpiperidine, 4-benzylpiperidine, 3-benzylpiperidine, and 4-phenylpiperidine, in a solvent comprising a mixture of water and water-insoluable organic solvent under conditions of controlled pH and controlled water content to yield a compound of the formula

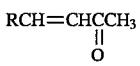

wherein R has the meaning of $R^1$.

4. Method according to claim 2 wherein the secondary amine catalyst is 3,5-dimethylpiperidine.

5. Method according to claim 3 wherein the secondary amine catalyst is 3,5-dimethylpiperidine.

6. Method according to claim 4 wherein the pH is controlled within the range of 6–8 with mineral acid.

7. Method according to claim 5, wherein the pH is controlled within the range of 6–8 with mineral acid.

* * * * *